United States Patent
Mitsugi et al.

(10) Patent No.: US 6,942,702 B2
(45) Date of Patent: Sep. 13, 2005

(54) STEM OF ARTIFICIAL HIP JOINT

(75) Inventors: Naoto Mitsugi, Kanagawa (JP);
Tomihisa Koshino, 28-12, Maruyamadai 2-chome, Konan-ku, Yokohama-shi, Kanagawa (JP), 233-0013

(73) Assignee: Tomihisa Koshino, Kanagawa (JP)

(*) Notice: Subject to any disclaimer, the term of this patent is extended or adjusted under 35 U.S.C. 154(b) by 0 days.

(21) Appl. No.: 10/298,221

(22) Filed: Nov. 18, 2002

(65) Prior Publication Data

US 2003/0097184 A1 May 22, 2003

(30) Foreign Application Priority Data

Nov. 21, 2001 (JP) ........................................ 2001-355470

(51) Int. Cl.$^7$ ................................................ A61F 2/32
(52) U.S. Cl. ................................................... 623/23.19
(58) Field of Search ................................. 623/22.11, 23.15, 623/23.19, 23.2, 23.26, 23.29, 23.3, 23.31

(56) References Cited

U.S. PATENT DOCUMENTS

| | | | | |
|---|---|---|---|---|
| 3,939,498 A | * | 2/1976 | Lee et al. | 623/23.27 |
| 4,888,022 A | * | 12/1989 | Huebsch | 623/22 |
| 4,892,550 A | * | 1/1990 | Huebsch | 623/23.19 |
| 5,116,377 A | * | 5/1992 | Skripitz et al. | 623/23 |
| 5,133,767 A | * | 7/1992 | Frey et al. | 623/23.54 |
| 5,133,772 A | * | 7/1992 | Hack et al. | 623/23 |
| 5,171,289 A | * | 12/1992 | Tornier | 623/22.44 |
| 5,181,928 A | * | 1/1993 | Bolesky et al. | 623/22.42 |
| 5,376,123 A | * | 12/1994 | Klaue et al. | 623/23 |
| 5,571,204 A | * | 11/1996 | Nies | 623/23 |
| 5,658,350 A | * | 8/1997 | Carbone | 623/23 |
| 5,725,586 A | * | 3/1998 | Sommerich | 623/23.35 |
| 5,755,810 A | * | 5/1998 | Cunningham | 623/22.44 |
| 5,807,407 A | * | 9/1998 | England et al. | 623/16 |
| 6,105,235 A | * | 8/2000 | Caldarise | 29/527.5 |
| 6,290,726 B1 | * | 9/2001 | Pope et al. | 623/22.15 |
| 6,599,322 B1 | * | 7/2003 | Amrich et al. | 623/23.5 |

* cited by examiner

*Primary Examiner*—Eduardo C. Robert
*Assistant Examiner*—David Comstock
(74) *Attorney, Agent, or Firm*—Nixon & Vanderhye P.C.

(57) ABSTRACT

A stem of an artificial hip joint is capable of removing a gap that may be formed between a proximal portion of a femur and a backside of the stem. The stem has an upper end portion to face a proximal side and a backside to face a greater trochanter and is adapted for insertion into, and fixation to, a medullary space of a femur. The stem has a through bore opened both to the upper end portion and the vicinity of proximal end of the backside.

6 Claims, 6 Drawing Sheets

STEM OF ARTIFICIAL HIP JOINT

FIELD OF THE INVENTION

The present invention relates to a stem of an artificial hip joint.

PRIOR ART

FIG. 5 shows one example of conventional artificial hip joint. The artificial hip joint has a stem 10 and a head 20. The stem 10 is fixed to a femur 30, and the head 20 is constituted of a ball 21 and a socket 22 to be fixed to a cotyle 41 of a pelvis 40. The stem 10 has an upper end portion 11 facing a proximal side of a human body, a rod 12 projecting obliquely upward is formed on the upper end portion 11, and the ball 21 is engaged with, and fixed to, the rod 12. The ball 21 is slidably engaged with the socket 22 to form a joint that performs a relative motion. The stem 10 has a flange 13 formed on an upper end of its side where the stem 10 faces a small trochanter 34 of the femur 30. Before the stem 10 is fixed, a proximal end (upper end) of the femur 30 is excised, to form an opening portion 32 in a medullary space 31.

Conventionally, the stem 10 of an artificial hip joint is fixed to the femur 30 by either a bone cement method using bone cement or a cement-less method using no bone cement.

In the method of using bone cement, bone cement 35 is charged into the medullary space 31 of the femur 30 as shown in FIG. 5, the stem 10 is inserted into the medullary space 31, and the stem 10 is bonded to the femur 30 with the bone cement 35.

In the cement-less method, the stem 10 is struck into the medullary space 31 of the femur 30, and the surface of the stem 10 is brought into intimate contact with the surface of the medullary space 31 so that the stem is frictionally fixed, as shown in FIG. 6. In this case, the stem 10 has a surface provided with a number of fine projections 14 by a method of forming a porous coating, and bone penetrates concaves among the fine projections with the growth of a bone, so that a sufficient bonding can be attained. Further, there is used the stem 10 having a form that fits the surface of medullary space 31 of the femur 30 as well as possible.

In the method using the bone cement 35, a considerable amount of the bone cement 35 is used, so that not only serious complications such as fat embolism, etc., are caused, but also the amount of a toxic decomposition product leaked from the cement 35 increases and may damage the bone. Further, a loosening occurs in an interface between the cement 35 and the femur 30 or in an interface between the stem 10 and the cement 35. Furthermore, curing of the bone cement takes a time, so that the time period of the operation increases.

In the cement-less method, the medullary space 31 is rasped with a broach in the operation. In some cases, particularly, there is employed the procedure of scraping off a portion of a greater trochanter 33 of the femur 30 with a broach for inserting the stem 10 having a proper size into the medullary space 31. The bone is sometimes scraped off to excess, so that a gap 32a is formed between the femur 30 and a backside 15 of the stem 10, and adhesion is liable to be lost. As a result, an early loosening is sometimes caused. Further, a friction powder, etc., generated by a relative motion between the ball 21 and the socket 22 enter the medullary space 31 through the gap 32a between the stem 10 and the femur 30, to cause osteolysis. Further, since no bone cement 35 is used, it takes several months to obtain a sufficient bonding of the femur 30 and the stem 10 to each other by bone growth, so that aftercare takes a long time.

SUMMARY OF THE INVENTION

It is an object of the present invention to provide a stem of an artificial hip joint that can remove a gap when the stem is fixed to a femur even if the gap is formed between a proximal portion of the femur and a backside of the stem.

It is another object of the present invention to provide a stem of a hip joint, which can attain a sufficient bonding of a femur and the stem without using a considerable amount of bone cement.

According to the present invention for achieving the above objects, there is provided a stem of an artificial hip joint, the stem having an upper end portion to face a proximal side and a backside to face a greater trochanter and being adapted for insertion into, and fixation to, a medullary space of a femur to be fixed, the stem having a through bore opened both to said upper end portion and the vicinity of proximal end of said backside. The through bore is used as an inlet for injecting bone cement, so that the gap between the backside of the stem and the proximal portion of the femur can be filled with the bone cement.

Typically, the above through bore is formed so as to be inclined.

As a stem, there can be employed a stem of an artificial hip joint that is for use in the conventional cement-less method, that is, a stem having a number of fine projections formed in the surface of its portion that is to be positioned between a greater trochanter and a small trochanter. In this case, the stem can be sufficiently bonded to a femur only with a small amount of bone cement.

PREFERRED EMBODIMENT OF THE INVENTION

Figure 1:
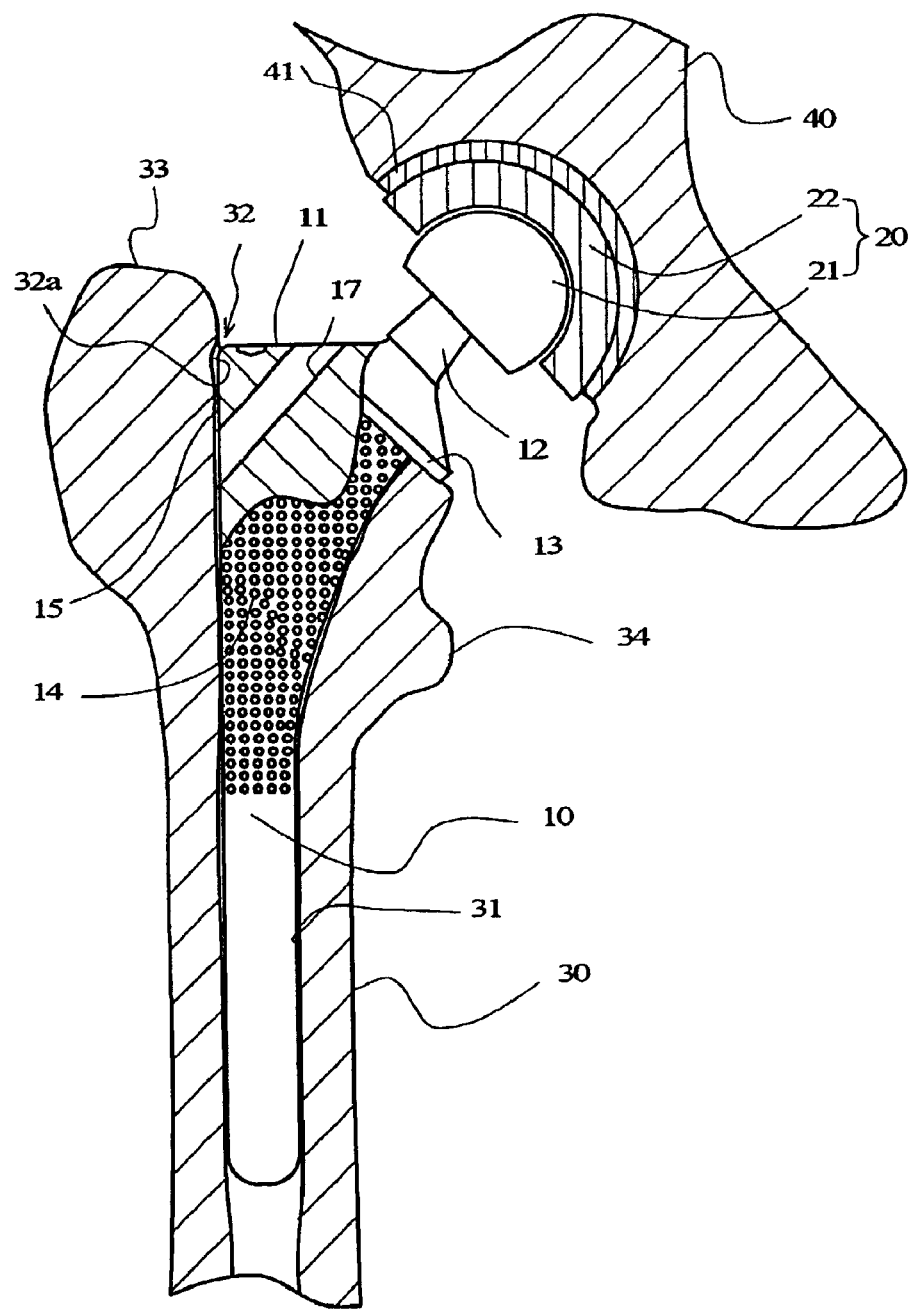
FIG. 1 is a cross-sectional view of a femur, etc., for showing an embodiment of the stem of an artificial hip joint provided by the present invention.
Figure 2:
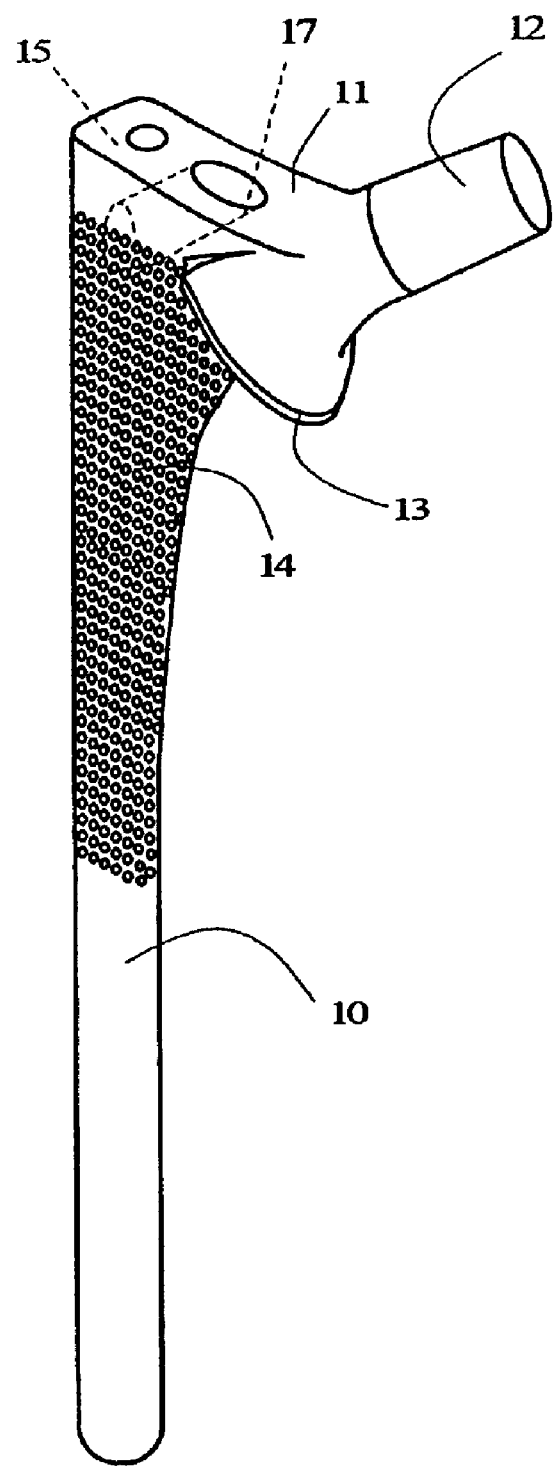
FIG. 2 is a perspective view of the embodiment of the present invention.
Figure 3:
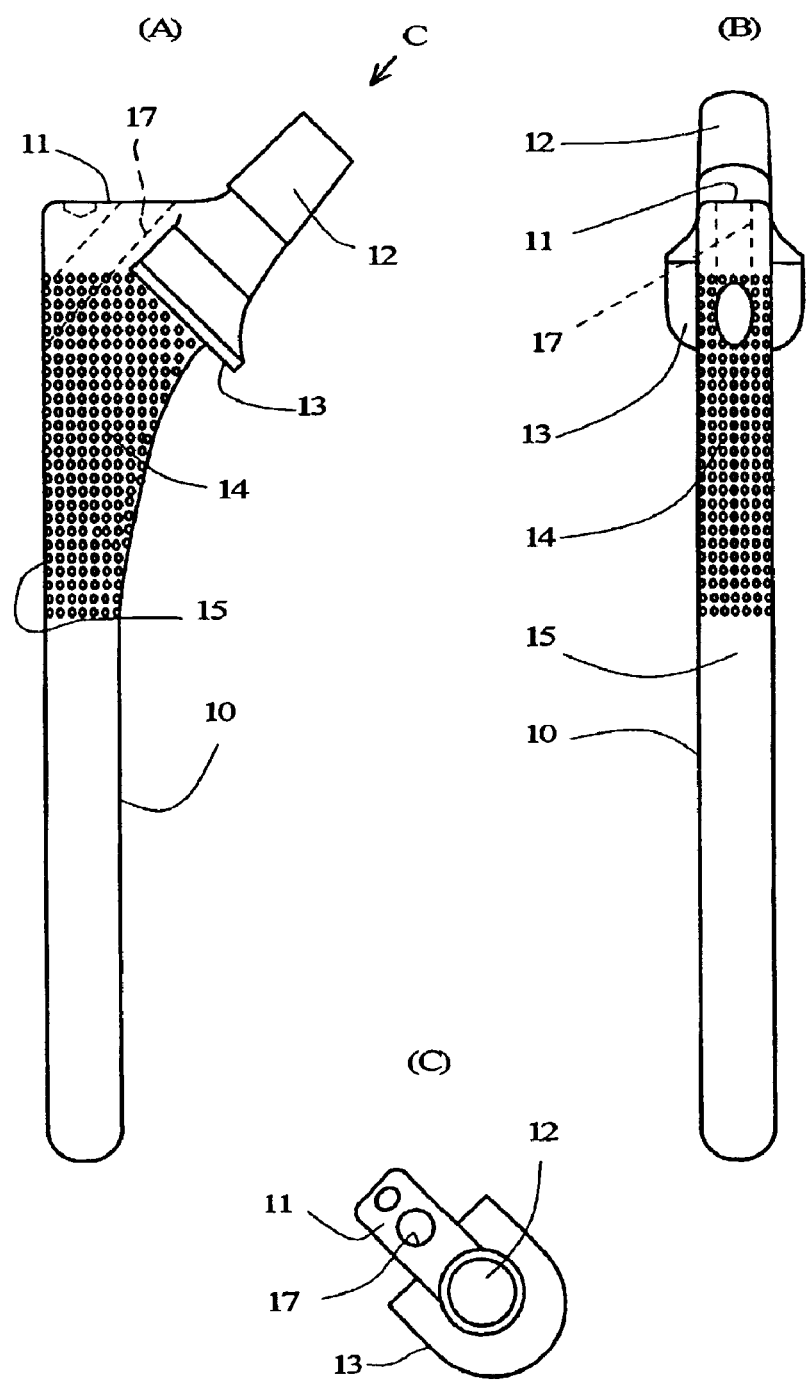
FIG. 3A is a front view of the embodiment of the present invention.
FIG. 3B is a side view of the embodiment of the present invention.
FIG. 3C is a top view of the embodiment of the present invention when the embodiment is seen in the direction of C in FIG. 3A.

The stem of an artificial hip joint according to the present invention will be explained with reference to FIGS. 1 to 4 hereinafter.

The artificial hip joint has a stem 10 and a head 20. The stem 10 is insertable into the medullary space 31 of a femur 30 to be fixed. The head 20 is constituted of a ball 21 and a socket 22, and the socket 22 is to be fixed to the cotyle 41 of a pelvis 40.

The stem 10 has an upper end portion 11 to face a proximal side of a human body and a backside 15 to face a greater trochanter 33. The upper end portion 11 has a rod 12 projecting obliquely upward. A ball 21 is engaged with, and fixed to, the rod 12. The ball 21 is slidably engaged with the socket 22, to form a joint that performs a relative motion. The stem 10 has a number of fine projections 14 formed on a surface of its portion that is to be positioned between a greater trochanter 30 and a small trochanter 33. The fine projections 14 are formed, for example, by plasma-spray-applied porous coating. The stem 10 has a flange portion 13 formed on its upper end that is to face the small trochanter 34 of a femur 30.

The stem 10 is provided with a through bore 17 that is inclined nearly in the same direction as the inclination direction of the rod 12. The through bore 17 is opened both to the upper end portion 11 and the backside 15, and an opening portion to the backside 15 is formed near the proximal end (upper end) of the stem 10.

The method of fixing the above-constituted stem 10 to a femur 30 will be explained below. First, a proximal end (upper end) of the femur 30 is subjected to excision to form an opening portion 32 in the medullary space 31. Then, the opening portion 32 is reamed with a reamer, and further, the medullary space 31 is rasped with a broach. As already described, the rasping sometimes involves the procedure of particularly scraping off a proximal outer side of the femur 30 (a portion of the greater trochanter 33) with a broach for inserting the stem 10 having a proper size into the medullary space 31. For the above reason or for some other reason, a gap 32a may be sometimes formed between the backside 15 of the stem 10 and the greater trochanter 33.

After completion of the rasping treatment, the stem 10 is struck into the medullary space 31 of the femur 30, and the surface of the stem 10 and the surface of the medullary space 31 are brought into an intimate contact with each other, so that the stem 10 and the femur 30 are frictionally fixed to each other. After the stem 10 is inserted into the medullary space 31, the flange portion 13 and the excision proximal end of the femur 30 come into contact with each other, to produce an effect that the femur 30 supports the stem 10.

Figure 4:
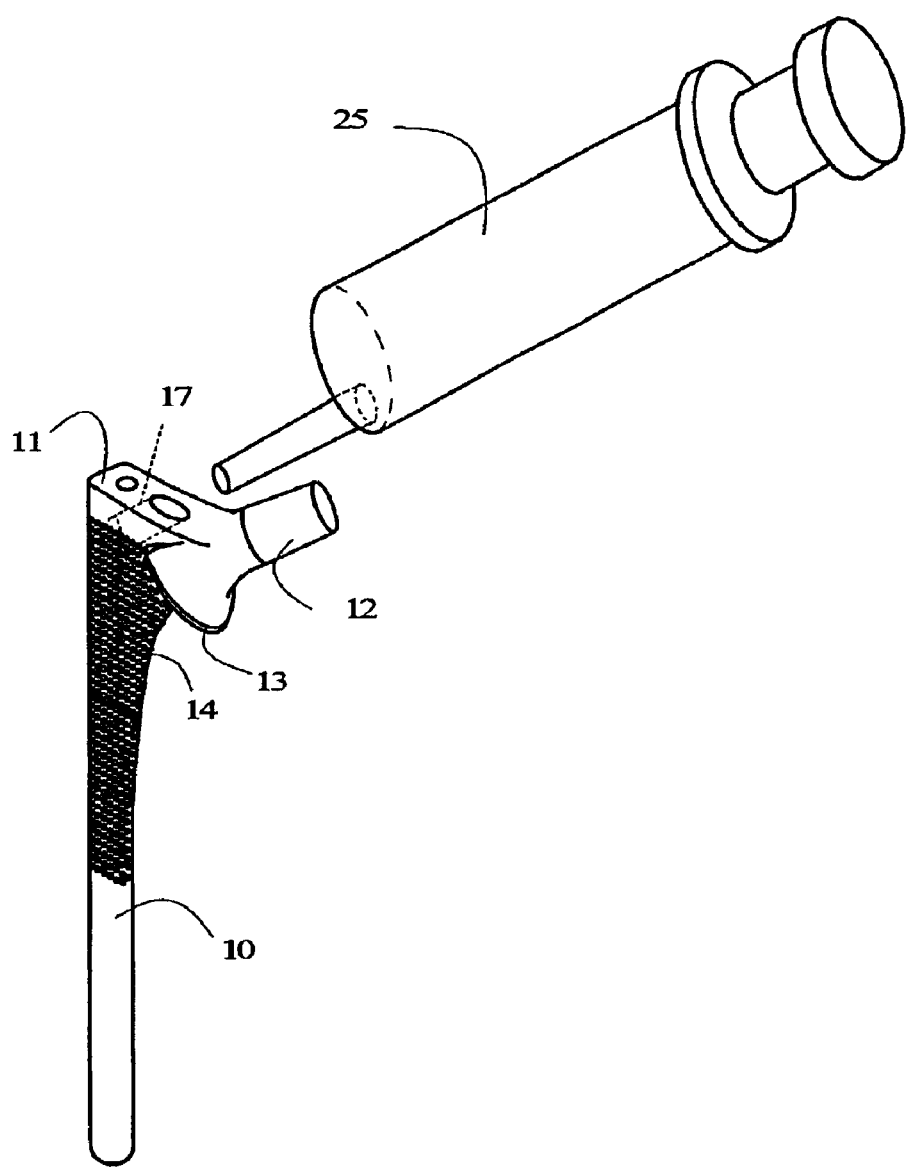
FIG. 4 is a perspective view of the stem of the embodiment of the present invention and a cement injector.
Figure 5:
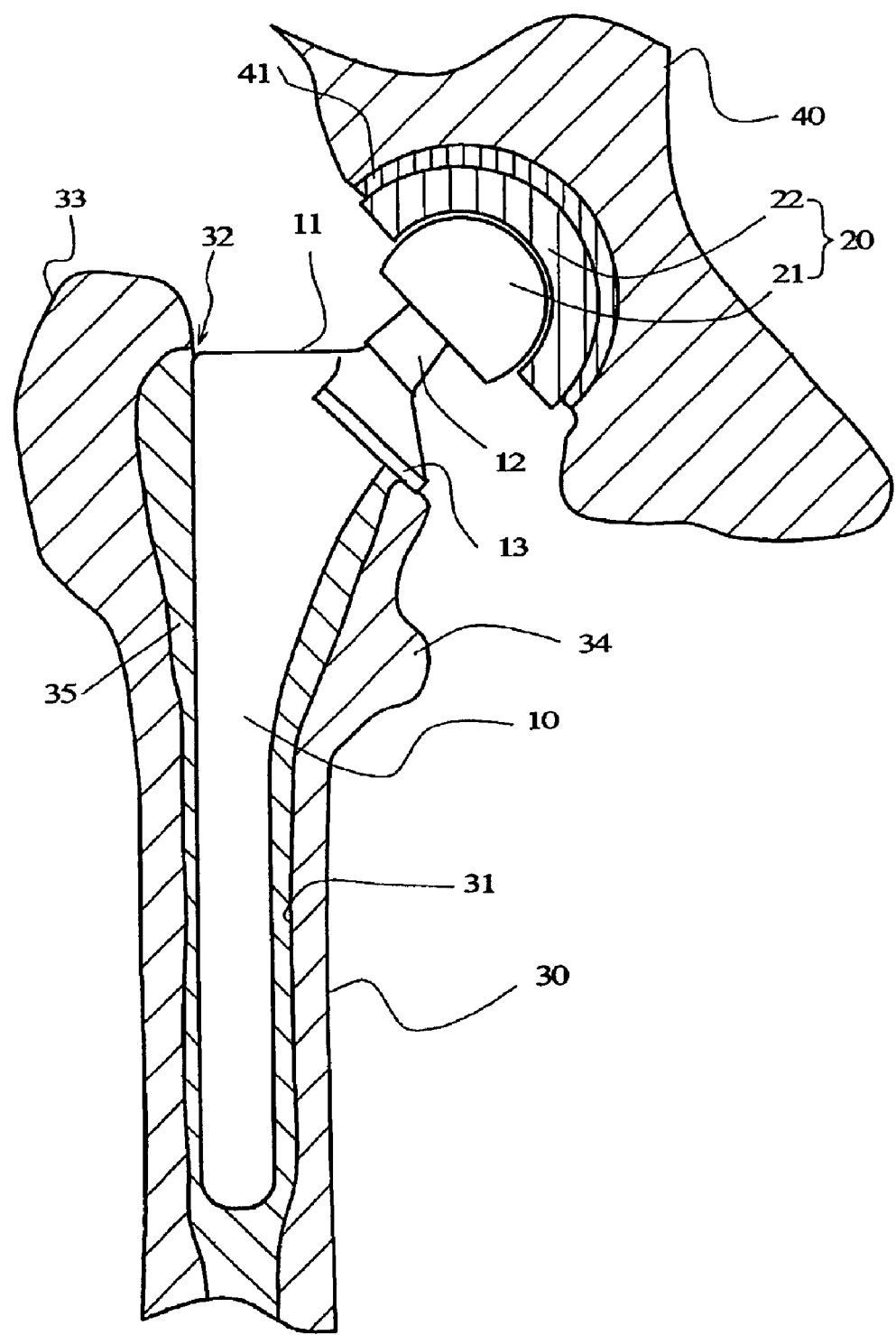
FIG. 5 is a cross-sectional view of one example of a conventional stem of an artificial hip joint.
Figure 6:
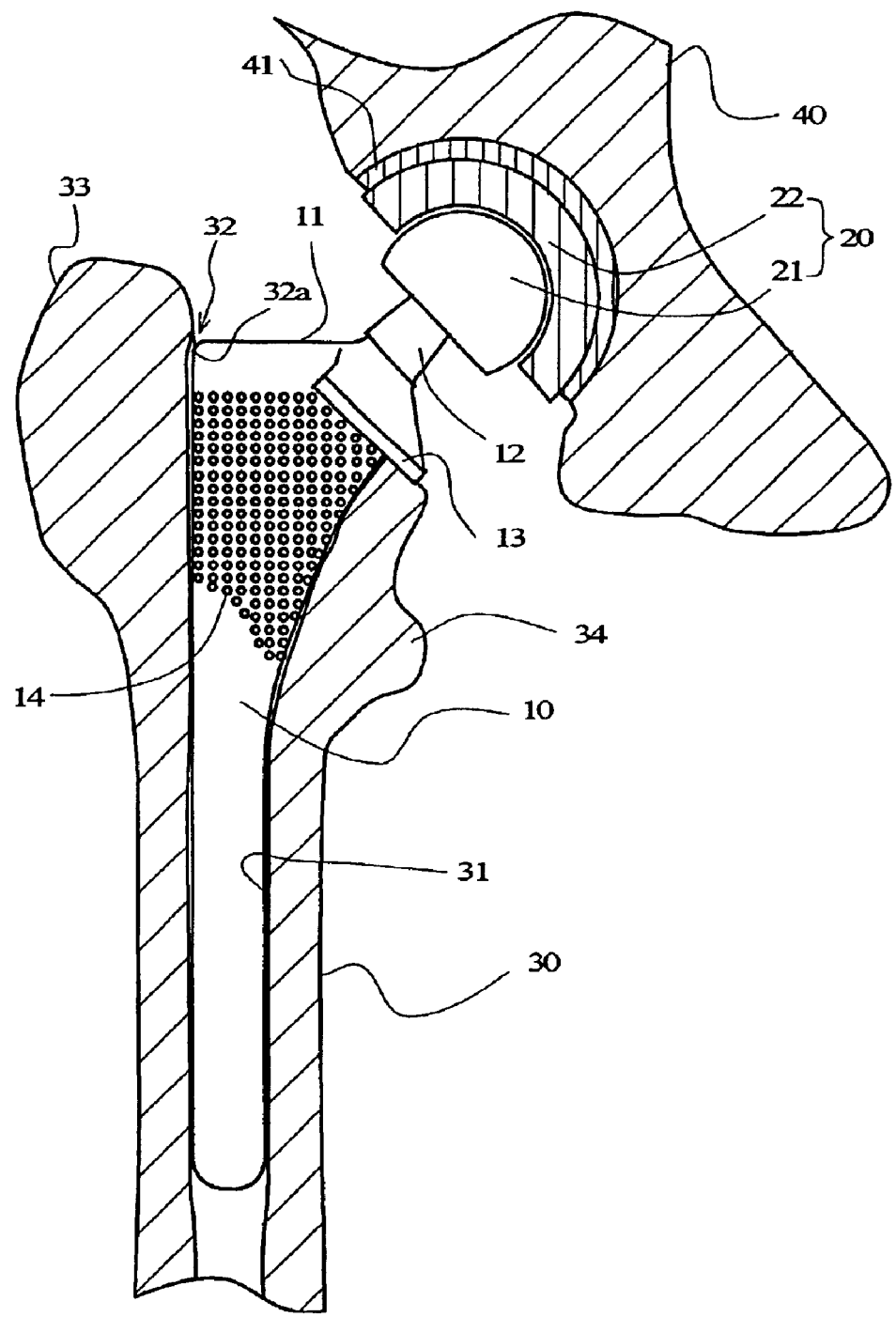
FIG. 6 is a cross-sectional view of another example of a conventional stem of an artificial hip joint.

Then, the forward end of a cement injector 25 shown in FIG. 4 is inserted into the through bore 17, and bone cement is injected, to fill the gap 32a between the backside 15 of the stem 10 and the greater trochanter 33. In this case, a proximal portion alone is fixed with the cement, so that only a small amount of the cement is used.

According to the stem 10 of the above embodiment of the present invention, not only the stem 10 can be sufficiently bonded to a femur only with a small amount of bone cement, but also the gap 32a between the backside of the stem 10 and the proximal portion of the femur can be filled with the bone cement.

The present invention shall not be limited to the above embodiment and may be changed or altered as required. For example, hydroxyapatite cement may be injected through the through bore 17 in place of the bone cement.

Further, while the above embodiment employs the method of forming a number of fine projections 14 on the surface of the stem 10 by plasma-spray applied porous coating, it shall not be limited thereto and may be any method so long as the fine projections 14 can be formed.

Furthermore, while the above embodiment shows the head 20 that is constituted of the socket 22 and the ball 21 which is slidably engaged with the socket 22, there may be employed a constitution in which two sliding parts are provided between the socket 22 and the rod 12, the socket 22 and a first sliding part perform a sliding motion, and the first sliding part and a second sliding part perform a sliding motion (bipolar type).

According to the present invention, there is provided a stem of an artificial hip joint, the stem having an upper end portion to face a proximal side and a backside to face a greater trochanter and being adapted for insertion into, and fixation to, a medullary space of a femur to be fixed, the stem having a through bore opened both to said upper end portion and the vicinity of proximal end of said backside. The through bore is used as an inlet for injecting bone cement, so that a gap between the backside of the stem and the proximal portion of a femur can be filled with the bone cement. There can be therefore overcome problems that a gap may be formed between a femur and the backside of a stem to lose adhesion, and that a friction powder enters a medullary space through the gap to cause osteolysis, which problems are caused in the conventional cement-less method.

When a stem having a number of fine projections formed on its surface to be positioned between a greater trochanter and a small trochanter, the above effects are naturally produced, and further, the stem can be sufficiently fixed to a femur only with a small amount of bone cement. The following problems caused due to the use of a considerable amount of bone cement can be therefore remarkably decreased. That is, there can be reduced problems of appearance of complications such as fat embolism, etc., detrimental effects of a toxic decomposition product leaked from the cement 35 on the bone, and a loosening that occurs in an interface between the cement and the bone or in an interface between the stem of an artificial hip joint and the bone cement. Further, there can be also overcome the problem that the operation takes a longer period of time since the curing of a considerable amount of a bone cement takes a longer time. There can be also overcome the problem caused in the conventional cement-less method, that is, the problem that aftercare may take a long time since it takes a time to obtain a sufficient bonding of a femur and the stem to each other by bone growth.

What is claimed is:

1. A stem of an artificial hip joint, the stem having an upper end portion to face a proximal side and a backside substantially perpendicular to the upper end portion to face a greater trochanter and being adapted for insertion into, and fixation to, a medullary space of a femur, the stem having a through bore with a first opening opened to said upper end portion and a second opening opened to said backside such that the first and second openings are substantially perpendicular to each other, wherein the through bore and the first and second openings are aligned, and wherein the first and second openings and the through bore are similarly sized, the stem being shaped and configured such that the second opening is positioned to directly face the greater trochanter when inserted into the medullary space.

2. The stem of an artificial hip joint as recited in claim 1, wherein said through bore is formed so as to be inclined.

3. The stem of an artificial hip joint as recited in claim 1, wherein the stem has a number of fine projections formed on its surface to be positioned between a greater trochanter and a small trochanter.

4. A stem of an artificial hip joint, the stem comprising:
   an upper end portion;
   a rod extending obliquely upward relative to the upper end portion; and
   a backside substantially perpendicular to the upper end portion to face a greater trochanter, wherein the stem is adapted for insertion into, and fixation to, a medullary space of a femur, the stem further comprising a through bore with a first opening opened to said upper end portion and a second opening opened to said backside such that the first and second openings are substantially perpendicular to each other, wherein the through bore is inclined throughout its length substantially aligned with the rod, and wherein the through bore and the first and second openings are similarly sized, the stem being shaped and configured such that the second opening is positioned to directly face the greater trochanter when inserted into the medullary space.

5. A stem of an artificial hip joint as recited in claim 4, wherein the stem has a number of fine projections formed on its surface to be positioned between a greater trochanter and a small trochanter.

6. A stem of an artificial hip joint, the stem having an upper end portion to face a proximal side and a backside substantially perpendicular to the upper end portion to face a greater trochanter and being adapted for insertion into, and fixation to, a medullary space of a femur, the stem having a through bore with a first opening opened to said upper end portion and a second opening opened to said backside such that the first and second openings are substantially perpendicular to each other, wherein the through bore and the first and second openings are aligned, wherein the first and second opening and the through bore are similarly sized, and wherein the stem is without structure that would interfere between the second opening and the greater trochanter when inserted into the medullary space.

* * * * *